United States Patent [19]
Lynt et al.

[11] Patent Number: 5,636,038
[45] Date of Patent: Jun. 3, 1997

[54] APPARATUS FOR CONVERTING VISUAL IMAGES INTO TACTILE REPRESENTATIONS FOR USE BY A PERSON WHO IS VISUALLY IMPAIRED

[76] Inventors: Ingrid H. Lynt; Christopher H. Lynt, both of 7502 Toll Ct., Alexandria, Va. 22306

[21] Appl. No.: 669,624

[22] Filed: Jun. 24, 1996

[51] Int. Cl.[6] .................... H04N 1/00; G09B 21/00
[52] U.S. Cl. ............... 358/471; 434/114; 345/31; 345/108; 345/110; 348/62; 340/825.19; 340/407.2
[58] Field of Search ............. 358/471; 434/113, 434/114; 345/31, 108, 110; 348/62; 340/407.1, 407.2, 825.19; 341/21

[56] References Cited

U.S. PATENT DOCUMENTS

| | | | |
|---|---|---|---|
| 3,229,387 | 1/1966 | Linvill | 434/114 |
| 3,594,787 | 7/1971 | Ickes | 340/407.1 |
| 4,250,637 | 2/1981 | Scott | 434/114 |
| 4,520,501 | 5/1985 | DuBrucq | 340/407.2 |
| 5,574,576 | 11/1996 | Martin | 434/114 |

*Primary Examiner*—Scott A. Rogers
*Attorney, Agent, or Firm*—Christopher H. Lynt

[57] ABSTRACT

A device for converting the visual and/or auditory into tactile representations includes imaging equipment for converting light and/or sounds, including spoken text, into electrical signals, processing equipment for processing the electrical signals, and a tactile display for converting processed electrical signals into tactile images. The tactile images are felt by the user enabling them to obtain visual or auditory information by touch about the world around them that would otherwise be obtained through vision and/or hearing.

16 Claims, 6 Drawing Sheets

AUXILLARY MINATURE MOTORS
RACK AND PINION ASSEMBLIES AND
RODS WHICH INDICATE COLOR

FIG. 5

APPARATUS FOR CONVERTING VISUAL IMAGES INTO TACTILE REPRESENTATIONS FOR USE BY A PERSON WHO IS VISUALLY IMPAIRED

BACKGROUND OF THE INVENTION

1. Field of the Invention

The invention relates to the field of imaging and robotic or machine implemented vision.

2. Background Information

Robotic vision is a growing field of research and development. Various image processing systems have been developed for guiding autonomous vehicles and the like through simple and complex obstacle courses. While robotic vehicles may be useful for transporting visually impaired individuals, they do not provide the individual with sensory information about the obstacles the robotic vehicle is navigating, nor control over the course the vehicle takes.

Visually impaired individuals are often able to self-navigate on foot through the use of various sensory clues, through the auditory, e.g., the sounds of traffic, or the tactile, e.g., the feel of objects tapped by a cane held in the hand. The sense of touch in a visually impaired individual may be heightened, and visually impaired individuals can "read" through the use of braille. If the person is also hearing impaired, the sense of touch may be additionally heightened.

SUMMARY OF THE INVENTION

It is an object of the invention to provide a visually impaired person with a tactile representation of the field of view of a sighted person, e.g., the objects in front of the individual and their respective spatial locations. The tactile representations will be referred to as "tactile images" herein.

The present invention provides the following novel features. According to one embodiment of the invention, imaging means converts light received from the field of view into electrical signals, processing means processes the electrical signals, and tactile display means converts the processed electrical signals into tactile images which can be perceived through the sense of touch by the visually impaired person. Therefore, the tactile images are felt by the visually impaired person and enable them to ascertain information by touch about the world around them that a sighted person would ascertain through vision.

According to another aspect of the invention, the imaging means comprises a portion of a robotic vision system, such as may include one or more high-resolution video cameras and an analog to digital convertor for converting an output signal of the cameras into a digital signal. The processing means could comprise memory means for storing the electrical signals as they are received from the imaging means, filtering means for adjusting features of the electrical signals, and output means for outputting the adjusted and stored electrical signals as processed electrical signals to control the tactile display means.

The tactile display means may comprise a plurality of individually controlled miniature actuators, e.g., motors or solenoids, oriented in a grid each of which respond to a portion of the processed electrical signals, a plurality of miniature gear assemblies, e.g., rack and pinion gear assemblies, each of which is operatively connected to one of the miniature actuators so that rotational motion of a pinion connected to a shaft of a miniature actuator is converted into linear motion of a rack, a plurality of rods, each of which is connected to one of the racks, so that when the racks move linearly, the rods move linearly as well, and means for adapting the tactile display means to a portion of the body of a visually impaired person including means for causing the rods to move perpendicular to the surface of the portion of the body. A tactile image is thus formed by the movement of the rods against the body of the person.

In another embodiment, a plurality of auxiliary miniature motors, rack and pinion assemblies and rods are provided which operate to indicate at least the color of light incident on the imaging means. Color could be indicated by a particular vibration of the rods so that a red traffic light would vibrate a group of rods at a certain frequency, while a green light would vibrate a group of rods at a different frequency.

In another embodiment, sounds may also be converted into tactile representations for use by a person who is also hearing impaired. This embodiment further comprises auditory imaging means for converting sounds into electrical signals, processing means for processing these electrical signals, and tactile display means for converting processed electrical signals into further tactile images. The further tactile images are felt by the hearing impaired person enabling them to ascertain information by touch about the world around them that a hearing person would ascertain through hearing. The further tactile images may be produced by tactile vibrations of at least a portion of the tactile display means.

In another embodiment, the apparatus further comprises speech analysis means, for detecting and recognizing spoken words, and outputting electrical signals to the processing means corresponding thereto. The processing means also processes the electrical signals from the speech analysis means, and the tactile display means also converts the processed electrical signals derived from the speech analysis means into further tactile images, the further tactile images being representations of the spoken words. In this way, the tactile images and further tactile images are felt by the visual and hearing impaired person enabling them to ascertain information by touch about the world around them that a sighted and hearing person would ascertain through vision and hearing. According to another aspect of the invention the further tactile images may be produced on a dedicated portion of the tactile display means.

In another embodiment, the processing means includes text means for processing scanned printed text, and the tactile display means includes text representation means for providing a tactile representation of scanned text processed by the processing means.

In an embodiment for converting sounds into tactile representations for use by a person who is hearing impaired, the apparatus includes auditory imaging means for converting sounds into electrical signals, processing means for processing the electrical signals, and tactile display means for converting processed electrical signals into tactile images. The tactile images are felt by the hearing impaired person enabling them to ascertain information by touch about the world around them that a hearing person would ascertain through hearing. In a further embodiment, the tactile images are representations of spoken words.

BRIEF DESCRIPTION OF THE DRAWINGS

The above and other features of the invention will become apparent from the following detailed description taken with the drawings in which:

FIG. 5 is a block diagram of an exemplary embodiment of the auxiliary display means according to the invention.

DETAILED DESCRIPTION OF THE PREFERRED EMBODIMENTS

The invention will now be described in more detail by example with reference to the embodiments shown in the Figures. It should be kept in mind that the following described embodiments is only presented by way of example and should not be construed as limiting the inventive concept to any particular physical configuration.

Figure 1:
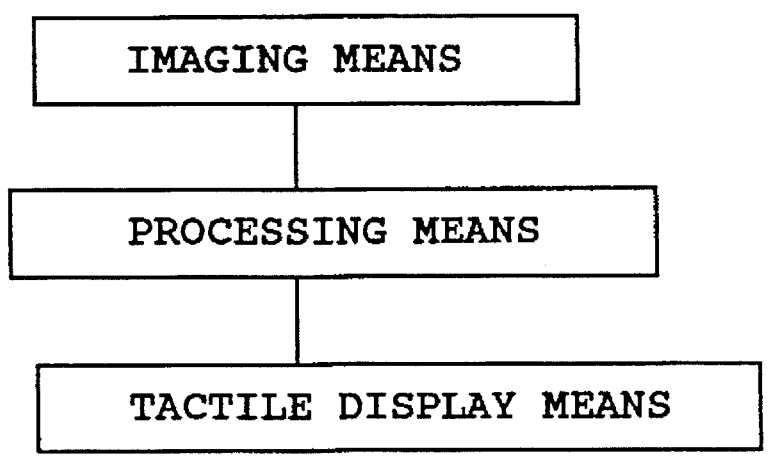
FIG. 1 is a block diagram of the major components of an exemplary embodiment of the invention.

FIG. 1 is a block diagram of the major components of an exemplary embodiment of the invention. Imaging means, which could take the form of one or more video cameras, CCD devices, or other light sensing devices, converts light into electrical signals and provides them to the processing means. The electrical signal may be analog or digital signals. To readily obtain depth information, at least two spatially separated video cameras would be used, as is well known in the art.

In applications where auditory information will be processed instead of, or in addition to, the visual, the imaging means would take the form of, or include, a microphone, or the like, and auditory amplifying, etc., circuitry.

The processing means processes the electrical signals from the imaging means. Such processing may include converting analog signals into digital signals and performing various well understood operations on the signals, such as performing a Fourier transform to extract object edge information, for example. The processing means in essence identifies objects, their relative size, their spatial location relative to the device, their movement, if any, etc.

If the imaging means is used to scan printed text, the processing means would include well known character recognition operations.

In the case of auditory information, filtering to extract spoken words or word segment (phonemes), for example, according to well know speech analysis techniques would be included.

The processing means together with the imaging means could take the form of a conventional robotic vision system, modified as necessary to obtain relevant information, and output signals for controlling the tactile display means, as would be understood by one skilled in the art.

The tactile display means converts the processed electrical signals from the processing means into so-called "tactile images." The tactile images may be felt by a visually impaired person enabling them to ascertain information by touch about the world around them that a sighted person would ascertain through vision. The tactile display means would be placed on a surface of the individual's body and would provide tactile stimulation to the surface of the individual's skin to form a representation of the view of the imaging means. For example, if the imaging means were viewing an apple, the tactile display means could form a 3-dimensional "tactile image" of the surface of the apple. This will be explained in more detail below.

Figure 2:
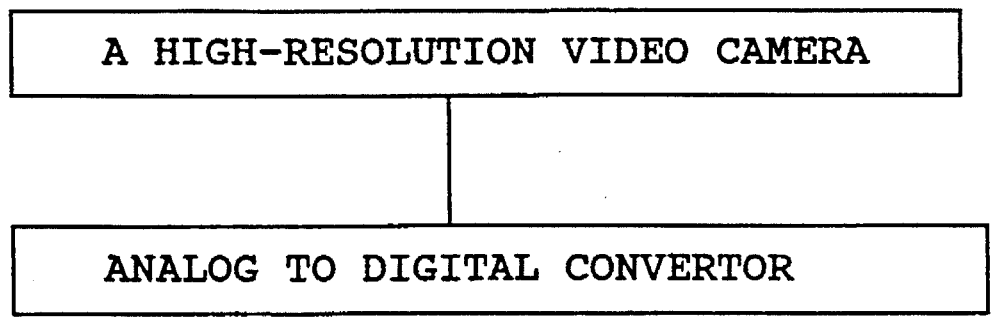
FIG. 2 is a block diagram of an exemplary embodiment of the imaging means according to the invention.

FIG. 2 is a block diagram of an exemplary embodiment of the imaging means according to the invention. In this embodiment, one or more high-resolution video cameras is connected to an analog to digital convertor to produce digital image signals. Other configurations would also work with the present invention, as would be readily apparent to one skilled in the art. To facilitate and simplify obtaining of depth information, a sonar device could be used instead of, or in conjunction with an optical imaging device.

Figure 3:
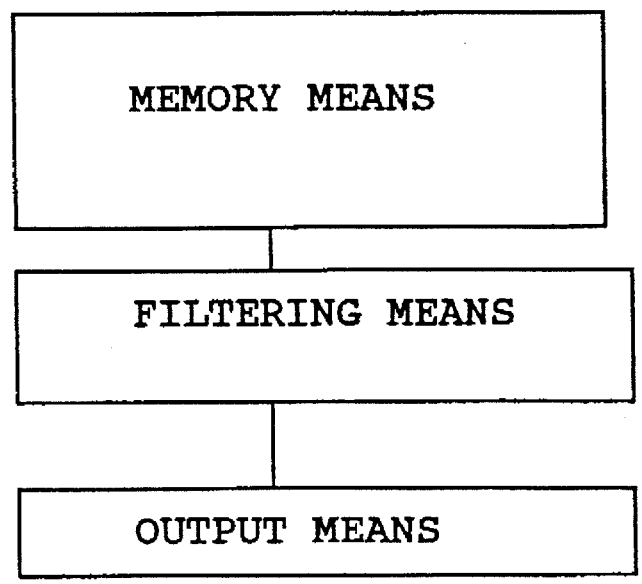
FIG. 3 is a block diagram of an exemplary embodiment of the processing means according to the invention.

FIG. 3 is a block diagram of an exemplary embodiment of the processing means according to the invention. Memory means would store electrical signals as they are received from the imaging means, and optionally, could perform some rudimentary or sophisticated matrix processing, for example, thereon. The memory means could take the form of a raster memory, for example.

Filtering means is provided to adjust features of the electrical signals stored in the memory means. The term "filtering" is used loosely to cover a variety of image data processing operations, such as fourier transform, convolution, and the like, to identify image features such as edges, shapes, size and relative spatial location, for example. The filtering means may comprise complicated special purpose digital processing integrated circuits, or be performed on a microprocessor under program control running digital signal processing routines.

A data base of common object patterns could be stored and accessed during this processing to identify ubiquitous objects, such as traffic lights, mail boxes, police cars, tanks, etc. There is a set of international symbols for various things, and through pattern recognition, these could be found and identified.

Where auditory information is being processed to extract and identify words or word segments from spoken words, for example, a set of speech analysis operations would, of course, be performed. These processing functions are similar but not identical to those used to process visual images, as is well known in the art. For example, instead of recognizing object edges, the processing word recognize periods of silence indicating the end of a word.

The output means outputs the "filtered" signals as processed electrical signals to operate the tactile display means so that image features are represented thereon as multi-dimensional "tactile images." The filtering means together with the output means function, for example, to identify an object, its shape and size, and then cause the tactile display means to form a tactile representation in multi-dimensions of the object. Since the tactile display means would, in general, be smaller than an object being imaged, the tactile representation would be scaled to relative size.

If the system should also provide color information, the output means and filtering means could cause the tactile display means to also indicate the color of the object, through a particular mechanical vibration for a particular color, for example. Auditory information could be indicated this way as well, such as the sound of machinery or traffic at an intersection.

Figure 4:
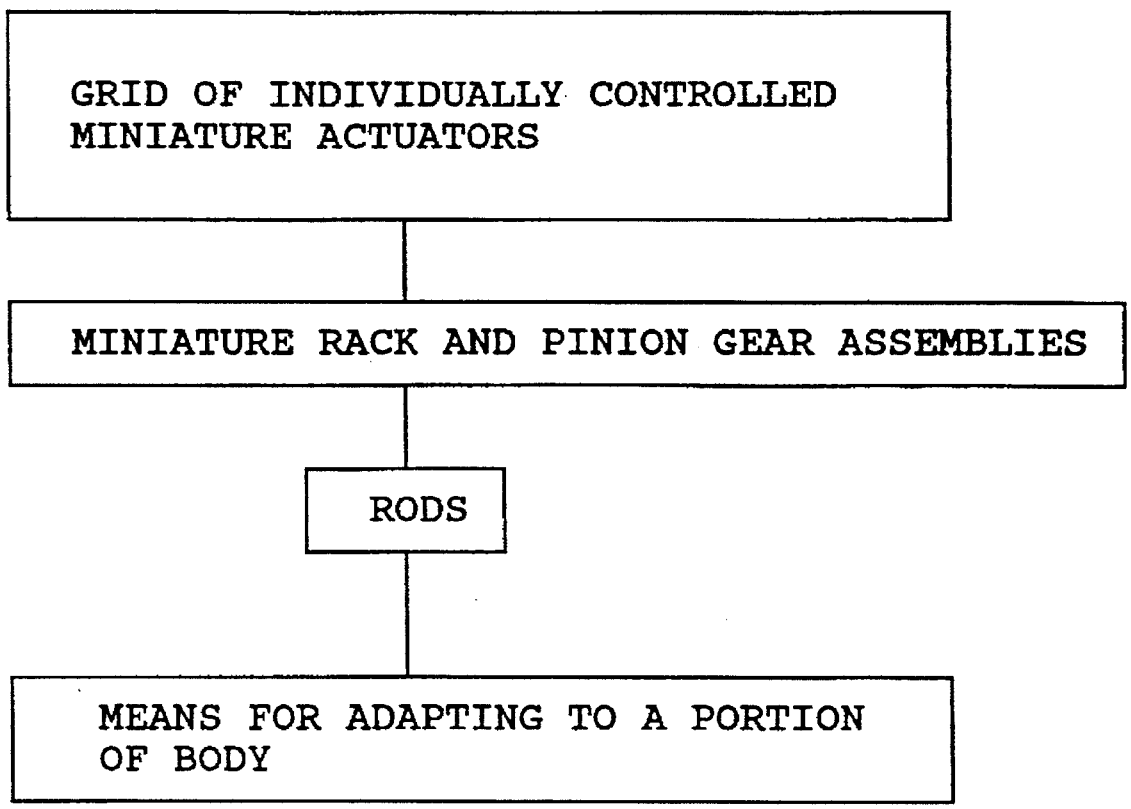
FIG. 4 is a block diagram of an exemplary embodiment of the tactile display means according to the invention.

FIG. 4 is a block diagram of an exemplary embodiment of the tactile display means according to the invention. In an exemplary embodiment, the display means could be formed as a two dimensional grid (X-Y dimensions) on which the individual would place their hand, for example. The surface of the grid would be formed by the ends of rods which would be moved up or down (Z dimension) under control of the processing means.

In more detail, in one embodiment, there is provided a plurality of individually controlled miniature motors oriented in a grid, each of which responds to a portion of the processed electrical signals. A plurality of miniature rack and pinion gear assemblies are also provided, each of which is operatively connected to one of the miniature motors so that rotational motion of a pinion connected to a shaft of a miniature motor is converted into linear motion of a rack. A plurality of rods form the surface of the tactile display, each of which is connected to one of the racks, so that when the racks move linearly, the rods move linearly as well. The relative linear motion of the individual rods forms a "tactile image." The motors could be formed by micro or nano-motors to produce very high resolution tactile images.

Means for adapting the tactile display means to a portion of the body of a visually impaired person may also be provided, and would include means for causing the rods to move perpendicular to the surface of the portion of the body. For example, the tactile display could be a two-dimensional grid in the shape of a hand or finger tip, for example. It does not necessarily have to be rectangular, for example.

For specialized applications, the display could be made spherical and about the size of a tennis ball, for instance. When held in the hand, and provided with 3-D information about an apple, for example, the sphere would take the three-dimensional form of the apple. In this embodiment, the rods would be extendable and retractable from a spherical initial position. In this embodiment, multiple imaging means, e.g., three cameras located in a triangulation arrangement, would be used, to obtain the three dimensional front, back and side information.

Thus, a tactile image is formed by the movement of the rods against the body (skin) of the person.

In a further embodiment according to the invention, as shown in FIG. 5, an auxiliary display means may be provided for indicating the color of the object, through a particular mechanical vibration for a particular color, for example. The output means and filtering means cause the tactile display through the auxiliary display means to also provide an indication of color. This could be used to indicate a red or green light signal, for example, or flashing yellow lights, which would be otherwise imperceptible to a vision impaired person.

Figure 6:
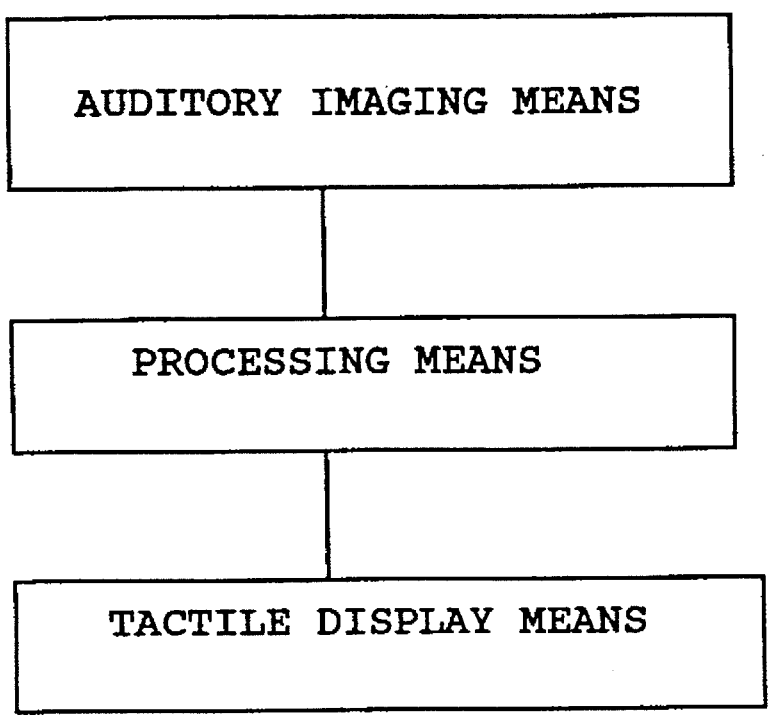
FIG. 6 is a block diagram of an exemplary embodiment of an apparatus for converting sounds into tactile representations for use by a person who is hearing impaired, including auditory means, according to the invention.

FIG. 6 is a block diagram of an exemplary embodiment of an apparatus for converting sounds into tactile representations for use by a person who is hearing impaired, including auditory means, according to the invention. Similarly to the image processing described above, sounds would be detected and processed to form a tactile image. If the processing includes speech analysis, for example, the tactile display could be caused to form alphabetical or braille type characters.

If used in conjunction with the imaging features, the auditory processing could indicated a general noise level, such as are used by non-sighted persons to detect traffic patterns, machinery, etc. A specific portion of the tactile display could be dedicated to imaging while another portion would be dedicated to auditory display. Alternatively, separate displays could be provided for each function.

It will be apparent to one of ordinary skill in the art that the manner of making and using the claimed invention has been adequately disclosed in the above-written description of the preferred embodiment taken together with the drawings.

It will be understood that the above description of the preferred embodiment of the present invention is susceptible to various modifications, changes, and adaptations, and the same are intended to be comprehended within the meaning and range of equivalents of the appended claims.

For example, instead of video cameras, sonar or radar, or a combination of the three could be used for imaging objects in the field of view in question.

Besides displaying tactile images through the movement of mechanical rods, heat or vibration could be used, alone or in combination to indicate objects.

If a larger degree of processing power is provided, image identification along with a synthesized voice output could be used. For example, if the device could recognize a familiar object or person, the voice synthesizer could issue a spoken alert such as "mailbox" or "Mr. Bill" to the user.

Another application of the device could be as a hand-held text to braille reader. The imaging portion would be scanned over a printed document and the processing means would cause braille representations of the scanned text to be produced on the tactile display for sensing by the user.

If the imaging means is replaced or augmented with a listening device, i.e., a microphone, and the processing means includes speech analysis operations, the tactile display could be caused to output braille characters, or another representation, corresponding to detected speech. The device could be adapted to connect to a telephone so that tactile representations of speech received through the telephone are produced.

The device could also have applications for users who are not visually impaired but find themselves in conditions where visibility is limited. Sonar and/or radar imaging could here be used to "see" through fog and alert the person to object ahead through a tactile representation on the tactile display.

The invention thus covers a wide range of applications where transforming from the visual and/or auditory to the tactile has use. With advances in micro and nano-motor technology, tactile displays of extremely high sensitivity can be provided.

The device was initially envisioned as being used by sensory-limited individuals, however, other uses are considered to be within the scope of the invention.

What is claimed is:

1. An apparatus for converting visual images into tactile representations for use by a person who is visually impaired comprising:

imaging means for converting incident light into electrical signals;

processing means for processing the electrical signals; and tactile display means for converting processed electrical signals into tactile images;

whereby the tactile images are felt by the visually impaired person enabling them to ascertain information by touch about the world around them that a sighted person would ascertain through vision;

wherein the tactile display means comprises:

a plurality of individually controlled miniature motors oriented in a grid each of which respond to a portion of the processed electrical signals;

a plurality of miniature rack and pinion gear assemblies, each of which is operatively connected to one of the miniature motors so that rotational motion of a pinion connected to a shaft of a miniature motor is converted into linear motion of a rack;

a plurality of rods, each of which is connected to one of the racks, so that when the racks move linearly, the rods move linearly as well;

means for adapting the tactile display means to a portion of the body of a visually impaired person including means for causing the rods to move perpendicular to the surface of the portion of the body; whereby a tactile image is formed by the movement of the rods against the body of the person.

2. The apparatus of claim 1, wherein the imaging means comprises:

at least one high-resolution video camera; and an analog to digital convertor for converting an output signal of the at least one camera into a digital signal.

3. The apparatus of claim 1, wherein the processing means comprises:

memory means for storing the electrical signals as they are received from the imaging means;

filtering means for adjusting features of the electrical signals; and output means for outputting adjusted and stored electrical signals as processed electrical signals to the tactile display means.

4. The apparatus according to claim 3, wherein the processing means further comprises data base storing means for storing a data base of common object patterns and the international symbols thereof, the patterns including patterns representing:

a traffic signal light;

a mail box; and a police car;

wherein, the processing means compares the data base of common object patterns with the electrical signals from the imaging means for a match, and if a match is determined, outputs processed electrical signals of a corresponding international symbol to the tactile display means.

5. The apparatus according to claim 3, wherein the filtering means performs a Fourier transform to extract object edge information.

6. The apparatus of claim 1, wherein the tactile display means further comprises:

a plurality of auxiliary miniature motors, rack and pinion assemblies and rods which operate to indicate at least the color of the light incident on the imaging means.

7. The apparatus for converting visual images into tactile representations according to claim 1, wherein the processing means comprises:

matrix generation means for generating a matrix of data from the electrical signals, the matrix having an X and a Y dimension, and the data containing depth information; and wherein the tactile display means grid comprises an X-Y matrix of miniature motors corresponding proportionally to the matrix of data generated by the matrix generation means, the miniature motors being movable in a Z dimension, perpendicular to the X and Y dimensions, by an amount correspondingly proportional to the depth information contained in the data.

8. The apparatus according to claim 1, further for use by a visual and hearing impaired person, the apparatus further comprising:

auditory imaging means for converting sounds into electrical signals;

wherein the processing means also processes the electrical signals from the auditory imaging means; and wherein the tactile display means also converts the processed electrical signals derived from the auditory imaging means into further tactile images;

whereby the tactile images and further tactile images are felt by the visual and hearing impaired person enabling them to ascertain information by touch about the world around them that a sighted and hearing person would ascertain through vision and hearing.

9. The apparatus according to claim 8, wherein the further tactile images are produced by tactile vibrations of at least a portion of the tactile display means dedicated to providing the further tactile images.

10. The apparatus according to claim 1, further for use by a visual and hearing impaired person, the apparatus further comprising:

speech analysis means, for detecting and recognizing spoken words, and outputting electrical signals to the processing means corresponding thereto;

wherein the processing means also processes the electrical signals from the speech analysis means; and wherein the tactile display means also converts the processed electrical signals derived from the speech analysis means into further tactile images, the further tactile images being representations of the spoken words;

whereby the tactile images and further tactile images are felt by the visual and hearing impaired person enabling them to ascertain information by touch about the world around them that a sighted and hearing person would ascertain through vision and hearing.

11. The apparatus according to claim 10, wherein the further tactile images representing spoken words are produced on a dedicated portion of the tactile display means.

12. The apparatus according to claim 1, wherein the processing means comprises text means for processing scanned printed text; and wherein the tactile display means includes text representation means for providing a tactile representation of scanned text processed by the processing means.

13. The apparatus according to claim 4, further comprising:

auditory imaging means for converting sounds into additional electrical signals;

wherein the processing means is further for processing the additional electrical signals; and wherein the tactile display means is further for converting the additional processed electrical signals into additional tactile images;

whereby the additional tactile images can be felt by a hearing impaired person enabling them to ascertain information by touch about the world around them that a hearing person would ascertain through hearing.

14. The apparatus according to claim 13, wherein the tactile images are representations of spoken words.

15. The apparatus according to claim 1, wherein the imaging means comprises at least three cameras disposed in a triangular orientation about an object to be imaged; and wherein the tactile display means rods are disposed to define a spherical initial surface position approximately the size of a regulation tennis ball;

wherein the tactile display means rods retract or extend from the spherical initial surface position under control of the processing means to correspond approximately to the three-dimensional shape of an object being imaged.

16. The apparatus according to claim 1, further comprising distance and speed determining means for determining field of view objects distance and relative speed and producing electrical signals representative thereof to the processing means for processing.

* * * * *